United States Patent [19]
Sillman

[11] Patent Number: 5,916,150
[45] Date of Patent: Jun. 29, 1999

[54] SPECULUM FOR SIMULTANEOUSLY VIEWING AND REMOVING OBSTRUCTIONS

[76] Inventor: Jonathon S. Sillman, 8 Hayden Circle, Sudbury, Mass. 01776

[21] Appl. No.: 08/920,761

[22] Filed: Aug. 29, 1997

[51] Int. Cl.⁶ ................................................... A61B 1/227
[52] U.S. Cl. ........................................... 600/184; 600/200
[58] Field of Search ..................................... 600/184, 200, 600/114; 606/109

[56] References Cited

U.S. PATENT DOCUMENTS

| | | |
|---|---|---|
| 672,317 | 4/1901 | Dow . |
| 1,775,140 | 9/1930 | Platou . |
| 2,544,914 | 3/1951 | Cameron ................................. 600/184 |
| 3,020,912 | 2/1962 | Chester . |
| 3,110,304 | 11/1963 | Hartman . |
| 4,335,713 | 6/1982 | Komiya . |
| 4,572,180 | 2/1986 | Deenadayalu . |
| 4,641,663 | 2/1987 | Juhn ....................................... 128/765 |
| 4,766,886 | 8/1988 | Juhn . |
| 4,785,796 | 11/1988 | Mattson . |
| 4,913,132 | 4/1990 | Gabriel . |
| 5,390,663 | 2/1995 | Schaefer . |
| 5,392,764 | 2/1995 | Swanson et al. . |
| 5,665,094 | 9/1997 | Goldenberg . |
| 5,711,309 | 1/1998 | Goldenberg . |

FOREIGN PATENT DOCUMENTS

| | | |
|---|---|---|
| 1001807 | 3/1952 | France . |
| 2566668 | 1/1986 | France . |
| 3923851 | 8/1990 | Germany . |

*Primary Examiner*—Jeffrey A. Smith
*Attorney, Agent, or Firm*—Bromberg & Sunstein LLP

[57] ABSTRACT

An ear speculum is provided for use with a standard otoscope for simultaneously viewing and removing an obstruction from a patient's ear canal. Alternative embodiments can perform like functions in other body canals. Affixed to the speculum is a guide tube through which an elongated, flexible probe may be passed into the ear canal without hindering visibility through the speculum. Various embodiments of the flexible probe function to grasp, suction, or cut obstructions within the ear canal. Additionally, the speculum may be used in conjunction with an embodiment of the probe designed to puncture a patient's eardrum and collect a sample of middle ear fluid which is subsequently released into the ear canal.

19 Claims, 4 Drawing Sheets

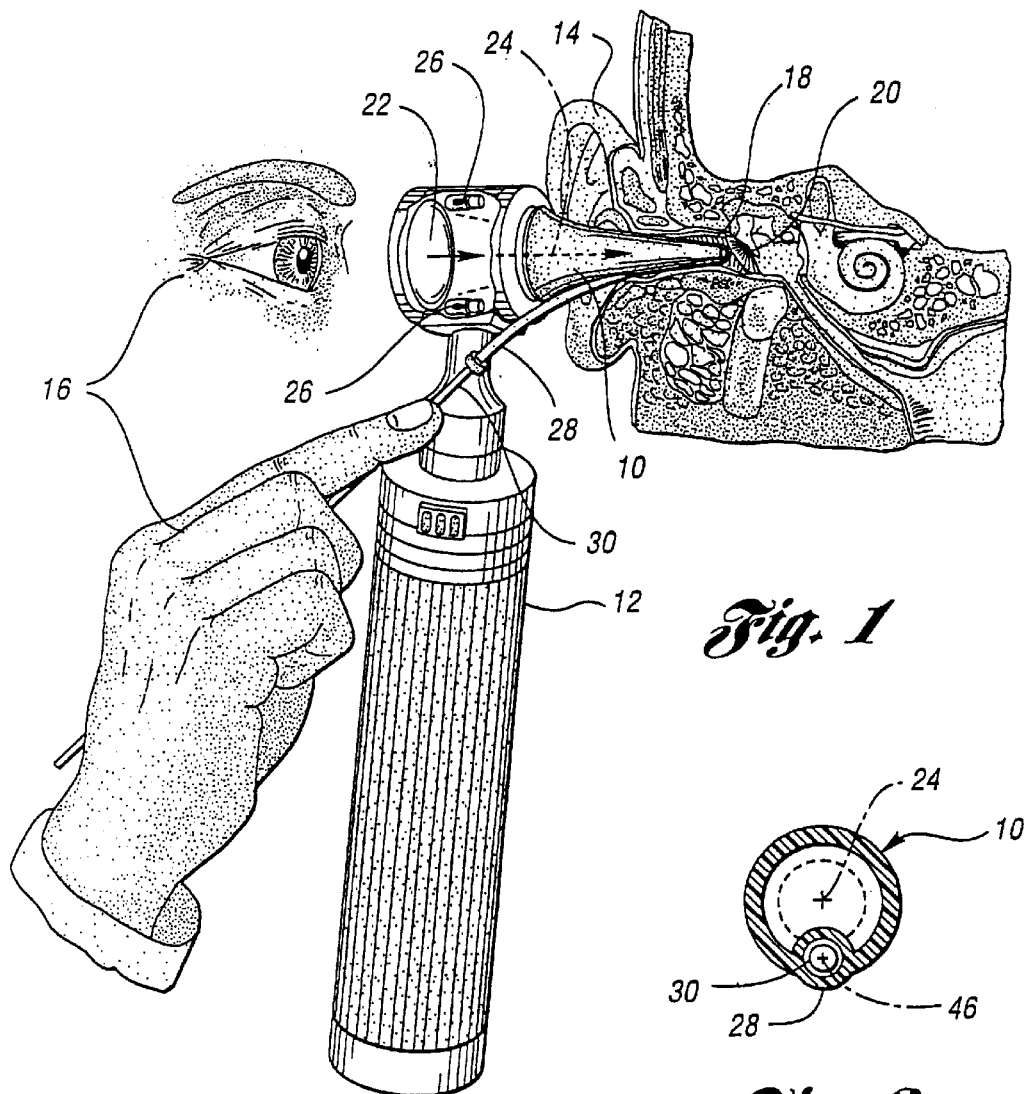
*Fig. 1*
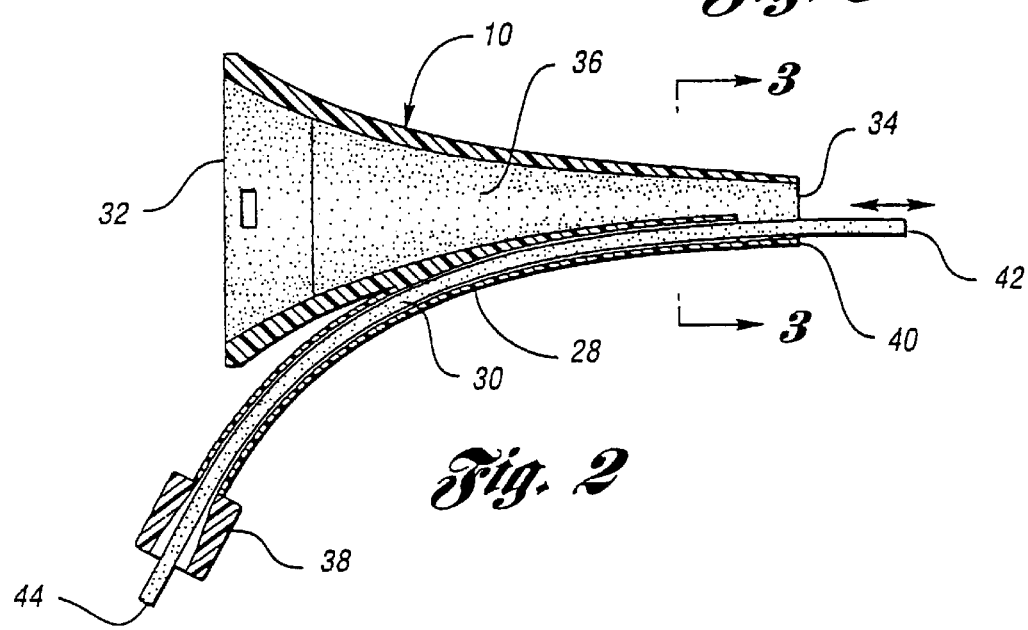
*Fig. 3*
*Fig. 2*

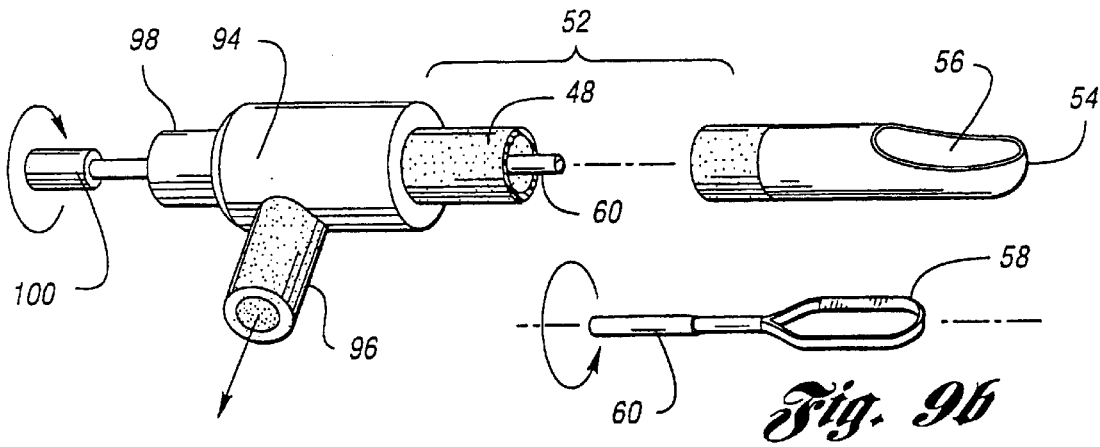
Fig. 9a
Fig. 9b
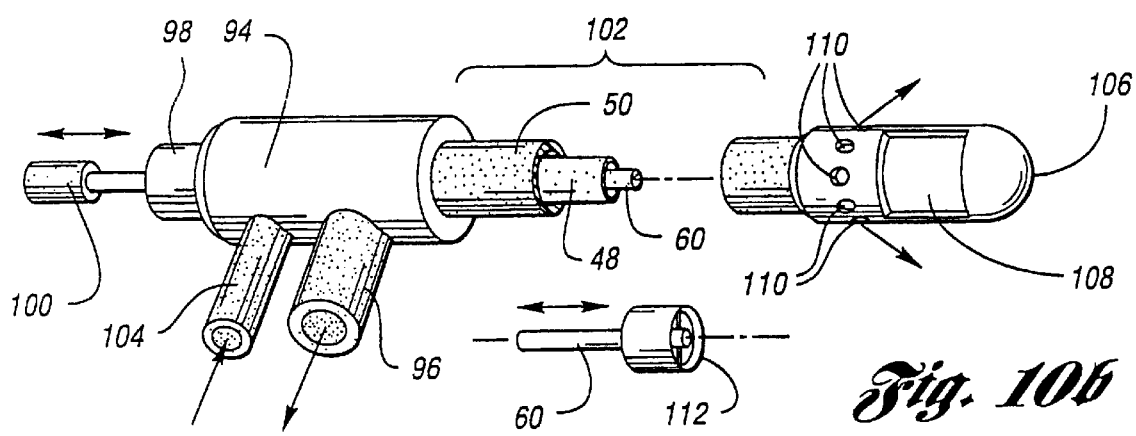
Fig. 10a
Fig. 10b
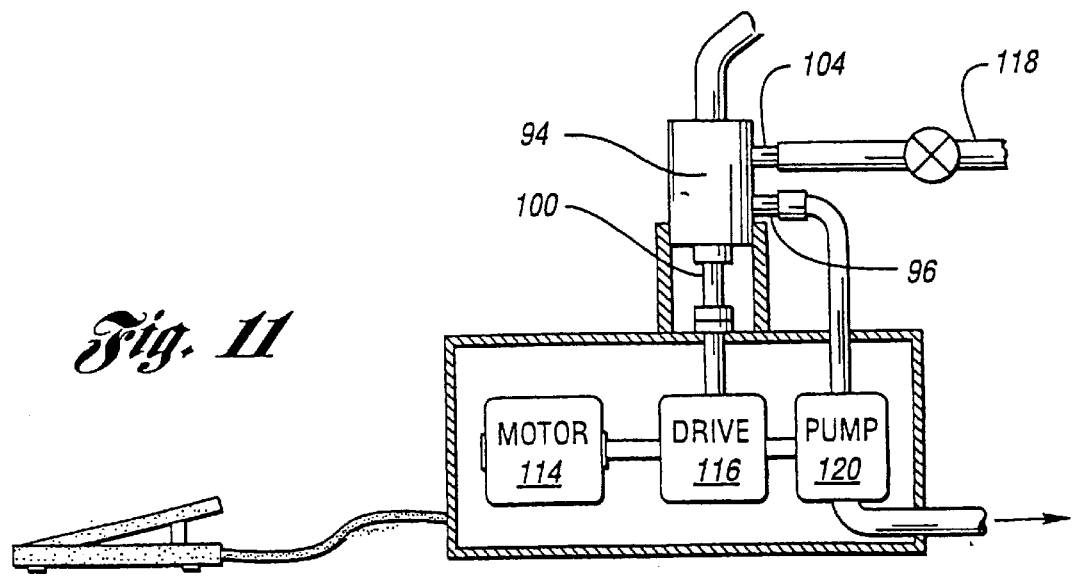
Fig. 11

SPECULUM FOR SIMULTANEOUSLY VIEWING AND REMOVING OBSTRUCTIONS

TECHNICAL FIELD

This invention relates to an ear speculum for use with a standard otoscope, and particularly to an ear speculum utilizing a guide tube affixed to the speculum through which probes may be passed in order to remove obstructions or fluid from the ear canal without hindering visibility through the speculum.

BACKGROUND ART

The otoscope is utilized by medical practitioners to examine a patient's ear canal and eardrum. In addition to examination procedures, medical practitioners use the otoscope as a visual aid when removing excessive ear wax or retrieving foreign objects lodged in a patient's ear canal. Standard otoscopes enable the medical practitioner to move the lens relative to the otoscope housing so that a thin probe can be inserted through the speculum to remove the obstruction. However, moving a lens off axis inherently hinders visibility, and the presence of a probe within the speculum further compromises the field of view. Clearly, a lack of direct visual observation during the procedure increases the risk of injury to the tissue of the ear canal and to the eardrum. The risk is further increased when examining and treating small children who are likely to become fearful and move about during the examination.

In addition to removing obstructions from the ear canal, medical practitioners employ the otoscope to diagnose and treat bacterial infections of the middle ear. Such an infection can be observed as a reddening and outward bulging of the eardrum associated with extensive fluid retention in the middle ear. It is often necessary for the medical practitioner to make a small incision in the eardrum, thus allowing the middle ear fluid to drain into the ear canal. Using a standard ear speculum, this procedure is made difficult due to limited visibility upon insertion of a needle through the speculum. Furthermore, the lack of a controlled needle insertion distance risks damage to middle ear structures. Due to the delicate nature of this procedure, a general anesthetic may even be required.

In treating acute infections of the middle ear, an antibiotic is often prescribed. Typically, the antibiotic mused has broad characteristics enabling the treatment of a wide variety of bacterial infections. However, due to the increasing emergence of antibiotic resistant bacteria, it is advantageous for the medical practitioner to be able to administer an antibiotic specific to the patient's particular bacterial infection. In order to select the appropriate antibiotic, the medical practitioner must obtain a sample of middle ear fluid to be submitted for culture. Once again, this procedure is complicated by the use of probes in connection with the standard ear speculum and furthermore by the lack of an effective sampling device.

Typical otoscopes, in which instruments designed to remove obstructions from the ear canal are inserted directly through the ear speculum, are shown in U.S. Pat. No. 1,775,140 to Platou and U.S. Pat. No. 3,020,912 to Chester. Such an otoscope wherein a sampling needle can be inserted through the speculum is shown in U.S. Pat. No. 4,766,886 to Juhn. U.S. Pat. No. 5,390,663 to Schaefer discloses an ear speculum provided with a protrusion external to the speculum having a free end which is articulated in response to the movement of tensioning filaments. However, the invention of Schaefer is limited in that the free end of the protrusion functions only to cup ear wax or foreign objects against the protrusion.

DISCLOSURE OF THE INVENTION

It is an object of the present invention to provide an ear speculum for use with a standard otoscope which provides a guide tube through which a flexible probe may be inserted into a patient's ear canal without hindering visibility through the speculum.

It is another object of the present invention to provide a method for removing an obstruction from a patient's ear canal wherein a flexible probe is utilized and the ear canal and the probe may be viewed simultaneously.

It is a further object of the present invention to provide a probe capable of using irrigation and suction in order to remove an obstruction from a patient's ear canal.

It is a further object of the present invention to provide a probe capable of grasping an obstruction in order to remove the obstruction from a patient's ear canal.

It is a further object of the present invention to provide a probe capable of cutting an obstruction into a plurality of pieces in order to facilitate removal of the obstruction from a patient's ear canal.

It is another object of the present invention to provide a method for sampling fluid from a patient's middle ear wherein a flexible probe is utilized and the patient's eardrum and the probe may be viewed simultaneously.

It is a further object of the present invention to provide a probe capable of puncturing a patient's eardrum and subsequently sampling the middle ear fluid which is released.

It is a further object of the present invention to provide a safety mechanism to control the depth to which a patient's eardrum is punctured.

It is a further object of the present invention to provide a method to locally anesthetize the patient's eardrum prior puncturing the eardrum.

It is a further object of the present invention to provide a method for determining the specific bacteria present in the middle ear fluid.

Accordingly, an ear speculum is provided for use with an otoscope for guiding a flexible probe into a patient's ear canal while simultaneously viewing the ear canal and a distal end of the probe. The ear speculum comprises a generally frusto-conical shape having an enlarged proximal end which is removably attachable to the otoscope, a relatively smaller distal end sized to be inserted into the patient's ear canal, and a tapered tubular section extending therebetween which is aligned along a central viewing axis. A curved guide tube having a generally circular cross-section and a diameter of 3 to 6 mm is affixed to the tapered tubular section of the speculum. The guide tube has an open proximal end which is freely accessible and spaced from the speculum when the speculum is inserted into the ear canal. A distal end of the guide tube is adjacent the distal end of the speculum. The flexible probe is inserted into the guide tube proximal end such that the probe distal end extends beyond the guide tube distal end in order to perform procedures within the ear canal. Alternative embodiments can perform like functions in other body canals.

In one embodiment, the probe is equipped with suction and irrigation capabilities to aid in removing an obstruction from the ear canal. In an alternative embodiment, a distal end of the probe comprises a forceps extension for use in grasping an obstruction, while in another embodiment a cutting blade is housed within the probe distal end serving to cut the obstruction into a plurality of pieces prior to removal of the obstruction from the ear canal.

Additionally, a method and device are provided for puncturing a patient's eardrum and collecting a sample of middle ear fluid that is released into the ear canal. Utilizing the ear speculum and associated guide tube, a probe is inserted through the guide tube into the ear canal. The probe comprises a tubular member which has a proximal end to which a plunger mechanism is connected, a distal end to which an absorbent member is affixed, and a central region therebetween. An elongated guide wire extends within the tubular member, the wire having a proximal end attached to the plunger mechanism and a distal end provided with a needle adjacent the tubular member distal end. The wire is axially movable within the tubular member in order to advance the needle through the absorbent member and puncture the patient's eardrum. The absorbent member is capable of absorbing middle ear fluid released into the ear canal through the eardrum. Subsequently, the probe is withdrawn from the ear canal and at least a portion of the middle ear fluid collected in the absorbent member is utilized in a diagnostic test procedure.

In one embodiment, the absorbent member affixed to the probe distal end may be treated with a topical anesthetic prior to insertion into the ear canal in order to numb the patient's eardrum upon contact with the absorbent member. In another embodiment, the absorbent member may be removed for use in a diagnostic test procedure. In still another embodiment, the plunger mechanism connected to the proximal end of the probe is equipped with a mechanical stop to prevent excessive advancement of the needle through the patient's eardrum.

The above objects and other objects, features and advantages of the present invention are more readily understood from a review of the attached drawings and the accompanying specification and claims.

BRIEF DESCRIPTION OF THE DRAWINGS

FIG. 1 is a perspective view of a standard otoscope provided with an improved ear speculum as it is used to examine a patient's ear canal and eardrum.

FIG. 2 is a longitudinal section of the ear speculum with its integral guide tube and a flexible probe inserted through the guide tube.

FIG. 3 is a cross-sectional view of the ear speculum, guide tube and probe along line 3—3 of FIG. 2.

FIGS. 8a–8d illustrate a method for puncturing the eardrum and obtaining a sample of middle ear fluid.

FIG. 9a is a side perspective view of a motor-actuated probe equipped with suction capabilities.

FIG. 9b is a side perspective view of a rotary loop blade used within a suction/irrigation probe.

FIG. 10a is a side perspective view of a motor-actuated probe equipped with both suction and irrigation capabilities.

FIG. 10b is a side perspective view of an annular sleeve blade used within a suction/irrigation probe.

FIG. 11 is a schematic representation of the motor and associated equipment used to operate the suction/irrigation probes depicted in FIG. 9a and FIG. 10a.

BEST MODE FOR CARRYING OUT THE INVENTION

Figure 4:
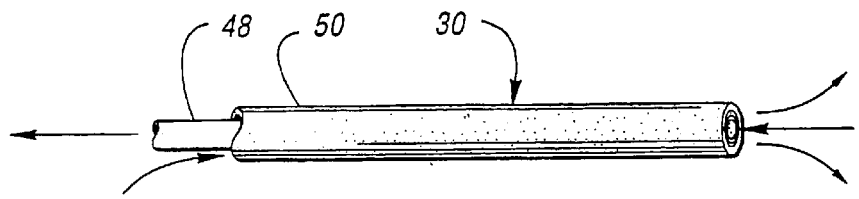
FIG. 4 is a side perspective view of the mid-section a probe used in suction and irrigation procedures.

Referring first to FIG. 1, an improved ear speculum 10 attached to a standard otoscope 12 is inserted into a patient's ear 14 by a medical practitioner 16 in order to examine an ear canal 18 and an eardrum 20. Medical practitioner 16 can view ear canal 18 and eardrum 20 through a magnifying lens 22 along a central viewing axis 24 aided by illumination from a light source 26 in standard otoscope 12. Affixed to ear speculum 10 is a guide tube 28 sized for the insertion of a flexible probe 30 through guide tube 28 and into ear canal 18. The orientation of guide tube 28 enables user 16 to view ear canal 18 and probe 30 simultaneously without requiring lens 22 to be moved off axis. Alternative embodiments of speculum 10 can perform like functions in other body canals such as, for example, the nasal passage.

FIG. 2 shows an enlarged, longitudinal view of ear speculum 10, associated guide tube 28, and flexible probe 30 inserted through guide tube 28. Ear speculum 10 is generally frusto-conical in shape, having an enlarged proximal end 32 that is removably attachable to standard otoscope 12, a relatively smaller distal end 34 for insertion into ear canal 18 (best shown in FIG. 1) and a tapered tubular section 36 therebetween. Guide tube 28 is curved and of generally circular cross-section, having a diameter of 3 to 6 mm. Guide tube 28 is affixed to tapered tubular section 36 of speculum 10 such that a proximal end 38 of guide tube 28 is freely accessible and spaced from speculum 10 when speculum 10 is inserted into ear canal 18 (best shown in FIG. 1).

Still referring to FIG. 2, guide tube 28 has a distal end 40 which is adjacent speculum distal end 34, wherein guide tube distal end 40 is open to speculum 10 for a distance of 4 to 5 mm at speculum distal end 34. This configuration allows for the removal via suction of obstructions, such as ear wax, which may block the entrance of ear canal 18 and would otherwise immediately occlude speculum 10. Guide tube proximal end 38 is outwardly flared to facilitate insertion of flexible probe 30, whereafter a distal end 42 of probe 30 can be extended past guide tube distal end 40 into ear canal 18. The configuration of guide tube 28 enables probe 30 inserted therethrough to be rotatable. By having probe distal end 42 slightly curved, rotation of a proximal end 44 of probe 30 will cause probe distal end 42 to move transversely within ear canal 18.

FIG. 3 is a cross-sectional view of ear speculum 10, guide tube 28 and probe 30. Guide tube 28 has a central axis 46 that is parallel to central viewing axis 24 of speculum 10 at guide tube distal end 40 (best shown in FIG. 2). The location of guide tube 28 enables probe 30 to be advanced through guide tube 28 without occluding central viewing axis 24.

FIG. 4 is an enlarged view of the mid-section of probe 30. As shown, probe 30 comprises an inner tube 48 and an outer tube 50 aligned coaxially. This configuration provides suction functionality via inner tube 48 and simultaneous irrigation functionality via outer tube 50. Although not illustrated, a simpler embodiment of probe 30 would comprise only inner suction tube 48 or only outer irrigation tube 50.

Figure 5:
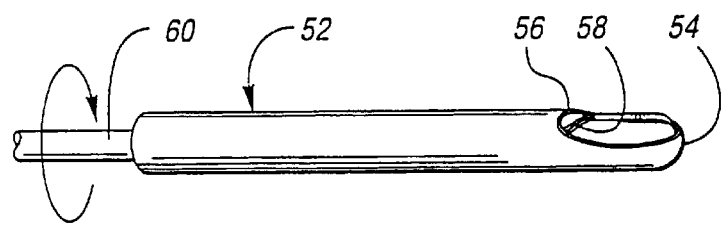
FIG. 5 is a side perspective view of the distal end of a probe which is equipped with a cutter blade.

FIG. 5 depicts a different probe 52 having a distal end 54 which is rounded to facilitate insertion into ear canal 18.

Probe distal end 54 is provided with a radial port 56 through which an obstruction may be evacuated. Adjacent radial port 56 is a rotary loop blade 58 which is connected to a drive wire 60 extending through probe 52. Upon rotation of drive wire 60, rotary loop blade 58 will rotate relative to radial port 56, thereby cutting an obstruction into a plurality of pieces and facilitating its evacuation.

Figure 6:
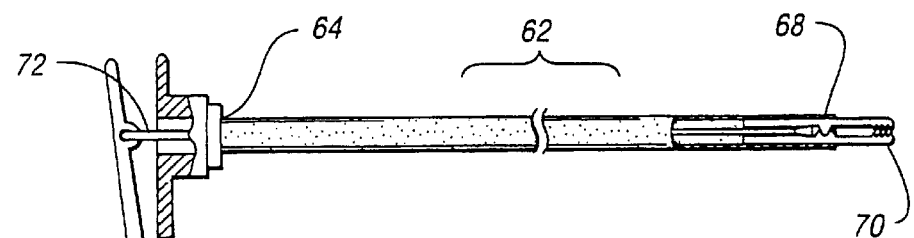
FIG. 6 is a side view of a probe used to grasp foreign objects within the ear canal, with a partial cutaway illustrating a forceps mechanism at the distal end.
Figure 6:

FIG. 6 shows an alternative probe 62 having a proximal end 64 which is freely accessible and connected to a scissor mechanism 66, a distal end 68 comprising a forceps extension 70, and guide wire 72 extending therebetween. Guide wire 72 acts to open and close forceps extension 70 in response to the opening and closing of scissor mechanism 66, thereby allowing forceps extension 70 to grasp an obstruction securely during its removal.

Figure 7:
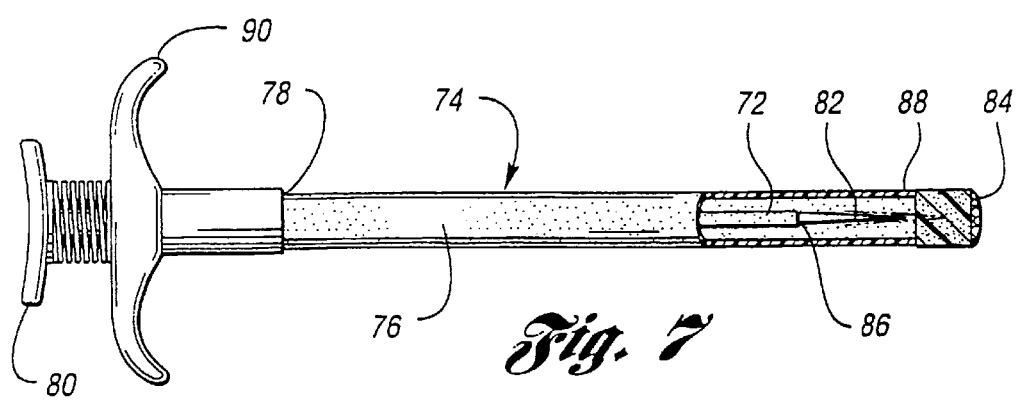
FIG. 7 is a side view of a probe used to puncture the eardrum and obtain a sample of middle ear fluid, with a partial cutaway illustrating a needle at the distal end.

FIG. 7 shows a probe 74 for use in diagnosing and treating a bacterial infection of the middle ear. Probe 74 comprises a tubular member 76 having a proximal end 78 to which a plunger mechanism 80 is connected, a distal end 82 to which an absorbent member 84 is removably attached, and guide wire 72 extending therebetween. Absorbent member 84 is 4 to 5 mm in length and 2 to 3 mm in diameter. Guide wire 72 has a distal end 86 provided with a needle 88 adjacent probe distal end 82 and may be axially advanced or retracted relative to tubular member 76 through use of plunger mechanism 80. Plunger mechanism 80 is provided with a mechanical stop 90 as a safety mechanism to limit advancement of needle 88 through absorbent member 84 to a distance of 2 mm beyond absorbent member 84. As illustrated in FIGS. 8a–8d, probe 74 may be used to puncture eardrum 20 and obtain a sample of middle ear fluid 92 that is released into ear canal 18.

Figure 8A:
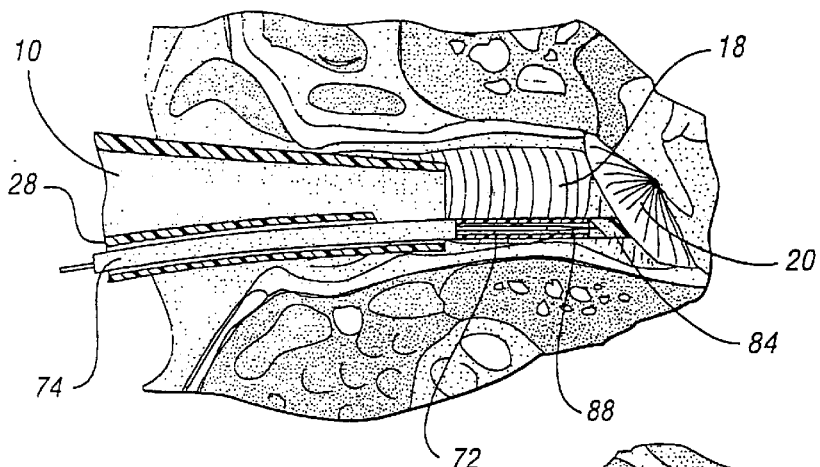
Figure 8B:
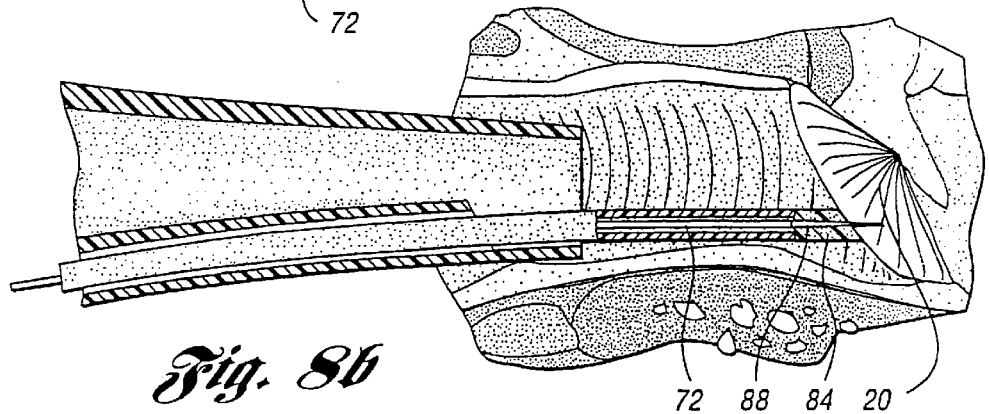

As shown in FIG. 8a, probe 74 is inserted through guide tube 28 affixed to ear speculum 10 into ear canal 18 adjacent eardrum 20. Absorbent member 84 is the first part of probe 74 to make contact with eardrum 20, thereby diminishing the risk of injury to eardrum 20 as opposed to an immediate introduction of needle 88. A topical anesthetic, such as phenol, may be applied to absorbent member 84 in order to numb eardrum 20 before insertion of needle 88. Once absorbent member 84 is in contact with eardrum 20, guide wire 72 and attached needle 88 are advanced, as illustrated in FIG. 8b, causing needle 88 to project through absorbent member 84 a controlled distance in order to puncture eardrum 20.

Figure 8C:
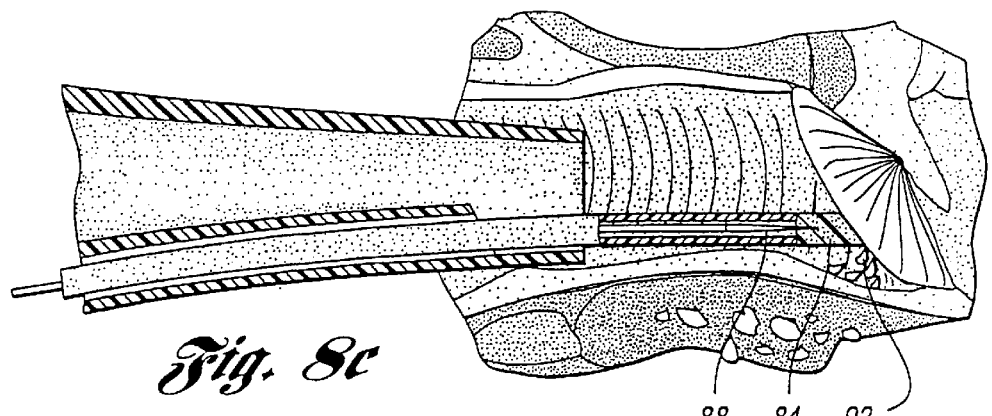
Figure 8B:
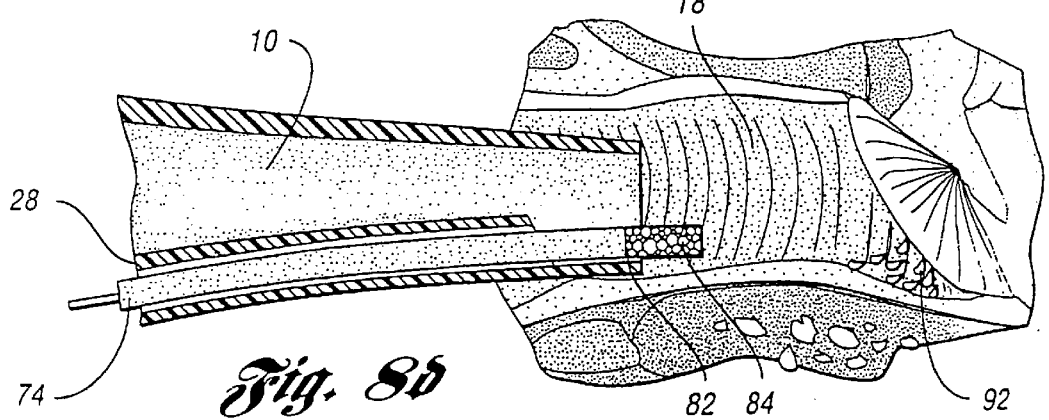

In FIG. 8c, needle 88 is retracted releasing middle ear fluid 92 through eardrum 20 into ear canal 18. Middle ear fluid 92 will be absorbed by absorbent member 84, as depicted in FIG. 8d. Probe 74 is withdrawn from ear canal 18 along with guide tube 28 and speculum 10, after which absorbent member 84 may be removed from probe distal end 82. Middle ear fluid 92 contained within absorbent member 84 can be analyzed by placing absorbent member 84 into culture media. Through this analysis, the specific bacteria present in middle ear fluid 92 may be determined, allowing a medical practitioner to select the particular antibiotic which will most effectively treat the infection.

FIG. 9a shows in greater detail probe 52 first illustrated in FIG. 5. Probe distal end 54 and associated radial port 56 are shown detached from the remainder of probe 52. A tubular member 94 houses suction tube 48 continuous with a suction outlet 96 adjacent a proximal end 98 of probe 52. Drive wire 60 extends through tubular member 94 to attach proximally to rotary loop blade 58, as depicted in FIG. 9b, and distally to an external drive attachment 100. Drive attachment 100 actuates a rotation of drive wire 60, causing rotary loop blade 58 to alternatively open and close radial port 56 as rotary loop blade 58 and tubular member 94 move relative to one another. An obstruction will be drawn into radial port 56 by suction and cut into a plurality of pieces by rotary loop blade 58 before evacuation through suction tube 48.

FIG. 10a shows a probe 102 which is an alternative embodiment of probe 52 depicted in FIG. 9a. In this embodiment, tubular member 94 is additionally provided with an irrigation inlet 104 connected adjacent suction outlet 96 continuous with outer irrigation tube 50. A distal end 106 of probe 102, shown detached from the remainder of probe 102, is rounded and provided with a squared radial port 108 as well as a plurality of outlet ports 110, wherein outlet ports 110 serve to dispense irrigation fluid into ear canal 18. Drive wire 60 extends through tubular member 94 to attach proximally to an annular sleeve blade 112, as depicted in FIG. 10b, and distally to drive attachment 100. In this embodiment, drive attachment 100 actuates an axial oscillation of drive wire 60, causing annular sleeve blade 112 to sequentially open and close radial port 108 as annular sleeve blade 112 is oscillated relative to tubular member 94. As above, an obstruction will be drawn into radial port 108 by suction and cut into a plurality of pieces by annular sleeve blade 112 before evacuation through inner suction tube 48.

FIG. 11 is a schematic representation of a motor 114 and an associated drive mechanism 116 used in conjunction with probe 52 (best shown in FIG. 9a) or probe 102 (best shown in FIG. 10a). Tubular member 94 is shown with suction outlet 96, irrigation inlet 104 connected to an irrigation source 118, and drive attachment 100. Drive attachment 100 is connected to drive mechanism 116, where drive mechanism 116 serves to actuate rotary loop blade 58 or annular sleeve blade 112 as well as a suction pump 120.

It is also understood, of course, that while the form of the invention herein shown and described constitutes a preferred embodiment of the invention, it is not intended to illustrate all possible forms thereof. It will also be understood that the words used are words of description rather than limitation, and that various changes may be made without departing from the spirit and scope of the invention disclosed.

What is claimed is:

1. An ear speculum for use with an otoscope for guiding an elongated, flexible probe into a patient's ear canal while simultaneously viewing the ear canal and a distal end of the probe, the ear speculum comprising:

a generally frusto-conical shape with an enlarged proximal end which is removably attachable to the otoscope, a relatively smaller distal end sized to be inserted into the ear canal, and a tapered tubular section extending therebetween which is aligned along a central viewing axis; and a guide tube affixed to the tapered tubular section of the speculum, the guide tube having an open proximal end which is freely accessible and spaced from the proximal end of the speculum when the speculum is inserted into the ear canal and a distal end adjacent the distal end of the speculum, the guide tube facilitating insertion of the flexible probe through the guide tube into the ear canal while simultaneously viewing the ear canal and the distal end of the probe extending beyond the distal end of the guide tube.

2. The invention of claim 1 wherein the proximal end of the guide tube is outwardly flared to facilitate insertion of the flexible probe.

3. The invention of claim 1 wherein the guide tube has a central axis which is parallel to the central viewing axis of the ear speculum at the distal end of the guide tube.

4. An ear speculum for use with an otoscope for guiding an elongated, flexible probe into a patient's ear canal while simultaneously viewing the ear canal and a distal end of the probe the ear speculum comprising:

a generally frusto-conical shape with an enlarged proximal end which is removably attachable to the otoscope, a relatively smaller distal end sized to be inserted into the ear canal, and a tapered tubular section extending therebetween which is aligned along a central viewing axis: and a guide tube affixed to the tapered tubular section of the speculum, the guide tube having an open proximal end which is freely accessible and spaced from the speculum when the speculum is inserted into the ear canal and a distal end adjacent the distal end of the speculum, the guide tube facilitating insertion of the flexible probe through the guide tube into the ear canal while simultaneously viewing the ear canal and the distal end of the probe extending beyond the distal end of the guide tube, the distal end of the guide tube being open and located a distance of between about 4 to 5 mm from the distal end of the speculum allowing for the removal of obstructions which may block the entrance of the ear canal.

5. An apparatus for use with a scope for guiding an elongated probe into a body orifice while simultaneously viewing both the orifice and a distal end of the probe, the apparatus comprising:

a speculum having an enlarged proximal end that is removably attachable to the scope, a distal end sized smaller than the proximal end for insertion into the body orifice, and a tubular section extending between the proximal end of the speculum and the distal end of the speculum; and a guide tube extending from the speculum and having an open proximal end and an open distal end, the proximal end of the guide tube being spaced from the speculum to facilitate insertion of the probe through the guide tube and into the body orifice.

6. The apparatus as defined by claim 5 wherein the distal end of the guide tube extends into the speculum.

7. The apparatus as defined by claim 5 wherein the speculum defines an interior, the distal end of the guide tube being in fluid communication with the interior of the speculum.

8. The apparatus as defined by claim 5 wherein the speculum defines an interior, the distal end of the guide tube extending into the interior of the speculum, the distal end of the guide tube being spaced from the distal end of the speculum within the interior.

9. The apparatus as defined by claim 8 wherein the distal end of the guide tube is spaced between about 4–5 mm from the distal end of the speculum.

10. The apparatus as defined by claim 8 wherein the distal end of the guide tube is spaced no closer than about 4 mm from the distal end of the speculum.

11. The apparatus as defined by claim 5 wherein the scope is an otoscope.

12. The apparatus as defined by claim 5 wherein the scope is an endoscope.

13. The apparatus as defined by claim 5 wherein the speculum is shaped generally frustoconically.

14. An apparatus for use with a scope for guiding an elongated probe into a body orifice while simultaneously viewing both the orifice and a distal end of the probe, the apparatus comprising:

a speculum having an enlarged proximal end that is removably attachable to the scope, a distal end sized smaller than the proximal end for insertion into the body orifice, and a tubular section extending between from the proximal end of the speculum and the distal end of the speculum, the speculum defining an interior; and a closed guide tube coupled to the speculum and having an open proximal end and an open distal end, the distal end of the guide tube being located within the interior of the speculum, the distal end of the guide tube being spaced from the distal end of the speculum within the interior of the speculum.

15. The apparatus as defined by claim 14 wherein the guide tube extends from the speculum.

16. The apparatus as defined by claim 14 wherein the proximal end of the guide tube is spaced from the speculum.

17. The apparatus as defined by claim 14 wherein the distal end of the guide tube is spaced between about 4–5 mm from the distal end of the speculum.

18. The apparatus as defined by claim 14 wherein the distal end of the guide tube is spaced no closer than about 4 mm from the distal end of the speculum.

19. The apparatus as defined by claim 14 wherein the speculum defines a view axis and the guide tube defines a central axis, the central axis being parallel to the view axis at the distal end of the guide tube.

* * * * *